United States Patent
Valenti et al.

(10) Patent No.: US 11,790,753 B2
(45) Date of Patent: Oct. 17, 2023

(54) SYSTEM AND METHOD FOR DETERMINING AND MANAGING SOCIALLY ISOLATED INDIVIDUALS

(71) Applicant: KONINKLIJKE PHILIPS N.V., Eindhoven (NL)

(72) Inventors: Giulio Valenti, Eindhoven (NL); Salvatore Saporito, Rotterdam (NL); Sabine Mollus, Juelich (DE)

(73) Assignee: Koninklijke Philips N.V., Eindhoven (NL)

(*) Notice: Subject to any disclaimer, the term of this patent is extended or adjusted under 35 U.S.C. 154(b) by 103 days.

(21) Appl. No.: 17/219,981

(22) Filed: Apr. 1, 2021

(65) Prior Publication Data

US 2021/0312784 A1  Oct. 7, 2021

Related U.S. Application Data

(60) Provisional application No. 63/005,617, filed on Apr. 6, 2020.

(51) Int. Cl.
*G08B 21/18* (2006.01)
*G16H 50/30* (2018.01)
(Continued)

(52) U.S. Cl.
CPC .......... *G08B 21/182* (2013.01); *A61B 5/1112* (2013.01); *A61B 5/165* (2013.01);
(Continued)

(58) Field of Classification Search
CPC ...... G08B 21/182; G08B 21/02; G16H 50/30; G16H 20/70; A61B 5/1112; A61B 5/165;
(Continued)

(56) References Cited

U.S. PATENT DOCUMENTS

| 8,335,473 B2 * | 12/2012 | Liao | H04W 24/00 726/2 |
| 8,943,138 B2 * | 1/2015 | Mallet | H04L 67/141 707/999.203 |

(Continued)

FOREIGN PATENT DOCUMENTS

WO 2015126851 A1 8/2015

OTHER PUBLICATIONS

International Search Report and Written Opinion, International Application No. PCT/EP2021/058391, dated Jun. 11, 2021.

*Primary Examiner* — Zhen Y Wu

(57) ABSTRACT

A method for monitoring the loneliness state of a subject includes receiving proximity information for a plurality of user devices and then generating a loneliness decision for subjects who use the devices based on the proximity information. In one case, the proximity information may be projected onto a lower dimensional space, distance values corresponding to the proximity information may be compared, and the user devices may be ranked based on the comparison. A user may then be determined to be lonely based on the ranking of the user devices. In other cases, clustering techniques may be applied relative to one or more centroids. Distances may then be calculated and compared for purposes of generating a loneliness decision. In other cases, resource information may be taken into consideration with distance information for generating a loneliness decision.

7 Claims, 11 Drawing Sheets

(51) Int. Cl.
*G16H 20/70* (2018.01)
*A61B 5/11* (2006.01)
*A61B 5/16* (2006.01)
*A61B 5/00* (2006.01)
*G08B 21/02* (2006.01)
*H04W 4/02* (2018.01)

(52) U.S. Cl.
CPC ............ *A61B 5/7275* (2013.01); *G08B 21/02* (2013.01); *G16H 20/70* (2018.01); *G16H 50/30* (2018.01); *H04W 4/023* (2013.01); *A61B 2562/0257* (2013.01)

(58) Field of Classification Search
CPC ......... A61B 5/7275; A61B 2562/0257; H04W 4/023
USPC ...................................................... 340/573.1
See application file for complete search history.

(56) References Cited

U.S. PATENT DOCUMENTS

| 9,668,117 | B2 | 5/2017 | Huang et al. | |
| 10,803,993 | B2* | 10/2020 | Huang | G16H 50/30 |
| 2012/0246244 | A1 | 9/2012 | Mallet | |
| 2012/0317064 | A1* | 12/2012 | Hagiwara | A61B 5/6898 |
| | | | | 706/46 |
| 2013/0281871 | A1* | 10/2013 | White | A61B 5/08 |
| | | | | 600/529 |
| 2014/0095618 | A1* | 4/2014 | Larson | G06Q 50/01 |
| | | | | 709/204 |
| 2014/0125493 | A1* | 5/2014 | Utter, II | G16H 20/30 |
| | | | | 340/870.02 |
| 2014/0129008 | A1* | 5/2014 | Utter, II | G16H 20/30 |
| | | | | 700/92 |
| 2014/0222954 | A1* | 8/2014 | Vaccari | G06Q 30/02 |
| | | | | 709/217 |
| 2014/0337451 | A1* | 11/2014 | Choudhary | A61B 5/22 |
| | | | | 709/206 |
| 2015/0099946 | A1* | 4/2015 | Sahin | A61B 7/04 |
| | | | | 600/301 |
| 2015/0172855 | A1* | 6/2015 | Mishra | H04W 4/029 |
| | | | | 455/418 |
| 2016/0142874 | A1* | 5/2016 | Jung | H04W 8/005 |
| | | | | 455/456.1 |
| 2018/0075763 | A1* | 3/2018 | Wainfan | G16H 20/70 |
| 2019/0209022 | A1 | 7/2019 | Sobol et al. | |
| 2021/0134469 | A1* | 5/2021 | Park | A61B 5/1118 |

* cited by examiner

SYSTEM AND METHOD FOR DETERMINING AND MANAGING SOCIALLY ISOLATED INDIVIDUALS

CROSS-REFERENCE TO PRIOR APPLICATIONS

This application claims the benefit of U.S. Provisional Application No. 63/005,617, filed on 6 Apr. 2020. This application is hereby incorporated by reference herein.

TECHNICAL FIELD

This disclosure generally relates to processing information, and more specifically to a system and method which apply a technological approach to determining and managing socially isolated individuals in a given area.

BACKGROUND

Interpersonal interactions play a vital role in psychophysiological wellbeing. When these interactions do not occur with any appreciable regularity, people may become lonely. Prolonged loneliness and social isolation have been linked to a wide range of physical and cognitive dysfunction, including dementia and other serious health conditions. This is especially true for the elderly, who, because of loneliness, often suffer a diminished quality of life lived out in a nursing home.

Because of the adverse effects of loneliness, psychosocial and wellbeing has become one of the key categories in the care area assessment (CAA) used by Medicare/Medicaid to certify and evaluate nursing homes. Attempts have been made to address these problems, by encouraging lonely people to get more involved through the use of social network links. However, these attempts are generalized or based on subjective observational assessments of caregivers and therefore have proven ineffective. Currently, there is no technical solution for objectively monitoring social interactions and identifying individuals experiencing loneliness for the purpose of improving quality of life.

SUMMARY

A brief summary of various example embodiments is presented below. Some simplifications and omissions may be made in the following summary, which is intended to highlight and introduce some aspects of the various example embodiments, but not to limit the scope of the invention. Detailed descriptions of example embodiments adequate to allow those of ordinary skill in the art to make and use the inventive concepts will follow in later sections.

In accordance with one or more embodiments, a method for managing information includes receiving proximity information for a plurality of user devices; projecting the proximity information into a lower dimensional space; comparing proximity of the user devices corresponding to the proximity information; ranking the user devices based on results of the comparison; and generating a loneliness decision for a user of at least one of the user devices based on the ranking of the user devices. The proximity information may include at least set of pair-wise distances values, and the pair-wise distances indicate distance estimated between a first user device of the plurality of user devices and remaining ones of the user devices of the plurality of user devices, respectively. The distance-pair values may be based on received radio frequency (RF) power.

Ranking the user devices may include assigning scores to the user devices based on results of the comparison, wherein each of the scores provides an indication of a social interaction pattern of a user of a corresponding one of the user devices in a monitoring area during a monitoring period. Generating the loneliness decision may include applying a threshold to the scores of the user devices, and determining that the user of at least one user device is at risk for loneliness based on the applied threshold.

Ranking the plurality of user devices may include receiving layout information for a monitoring area including the user devices, and assigning scores to the user devices based on results of the comparison and the layout information, wherein the layout information indicates at least one of a wall or room occupied by the user of the at least one user device. The method may include generating a notification indicating that the user of the at least one user device requires assistance to increase social interaction or requires a medical health evaluation.

In accordance with one or more embodiments, a method for managing information may include receiving proximity information for a plurality of user devices; generating clusters of the user devices based on the proximity information; locating first centroids of respective ones of the clusters; determining first distances of the user devices from the first centroids; identifying a second centroid of a monitoring area including the user devices; determining second distances of the user devices from the second centroid; generating social isolation scores for users of the user devices based on the first distances and the second distances; and generating a loneliness decision for a user of at least one of the user devices based on the social isolation scores. Each of the clusters may include spatially related groups of the user devices that corresponds to a successful interaction network.

The method may include performing a statistical analysis of at least one of the first distances or the second distances of the user devices, wherein generating the social isolation scores may include generating the social isolation scores based on results of the statistical analysis. The statistical analysis may include calculating a mean and standard deviation of at least one of the first distances or second distances. The method may include aggregating at least the second distances of the user devices from all of the clusters, wherein the social isolation scores are generated based on the aggregation of the at least second distances of the user devices.

Generating the loneliness decision may include applying a threshold to the social isolation scores of the user devices and determining that the user of at least one user device is at risk for loneliness based on the applied threshold. The method may include generating a notification indicating that the user of the at least one user device requires assistance to increase social interaction or requires a medical health evaluation. The social isolation scores may be generated based on layout information the monitoring area including the user devices and wherein the layout information indicates at least one of a wall or room occupied by the user of the at least one user device.

In accordance with one or more embodiments, a method for managing information includes receiving location information for a plurality of user devices; receiving resource information in a monitoring area including the user devices; quantifying a number of users corresponding to the user devices based on the location information and the resource information; forming clusters of the user devices based on the quantified number of user devices; determining types of the clusters; and generating a loneliness decision for a user of the at least one of the user devices based on the types of clusters. The types of clusters may include singular clusters and non-singular clusters.

Generating the loneliness decision may include determining that the user of at least one of the user devices is at risk for loneliness when the user is included in a singular cluster, and determining that the user of the at least one of the user devices is social interactive when the user is included in a non-singular cluster. The resource information may indicate a number of caregivers available in the monitoring area. The loneliness decision may be generated based on layout information the monitoring area and wherein the layout information indicates at least one of a wall or room occupied by the user of the at least one user device.

BRIEF DESCRIPTION OF THE DRAWINGS

The accompanying figures, where like reference numerals refer to identical or functionally similar elements throughout the separate views, together with the detailed description below, are incorporated in and form part of the specification, and serve to further illustrate example embodiments of concepts found in the claims and explain various principles and advantages of those embodiments.

These and other more detailed and specific features are more fully disclosed in the following specification, reference being had to the accompanying drawings, in which.

DETAILED DESCRIPTION

Figure 1:
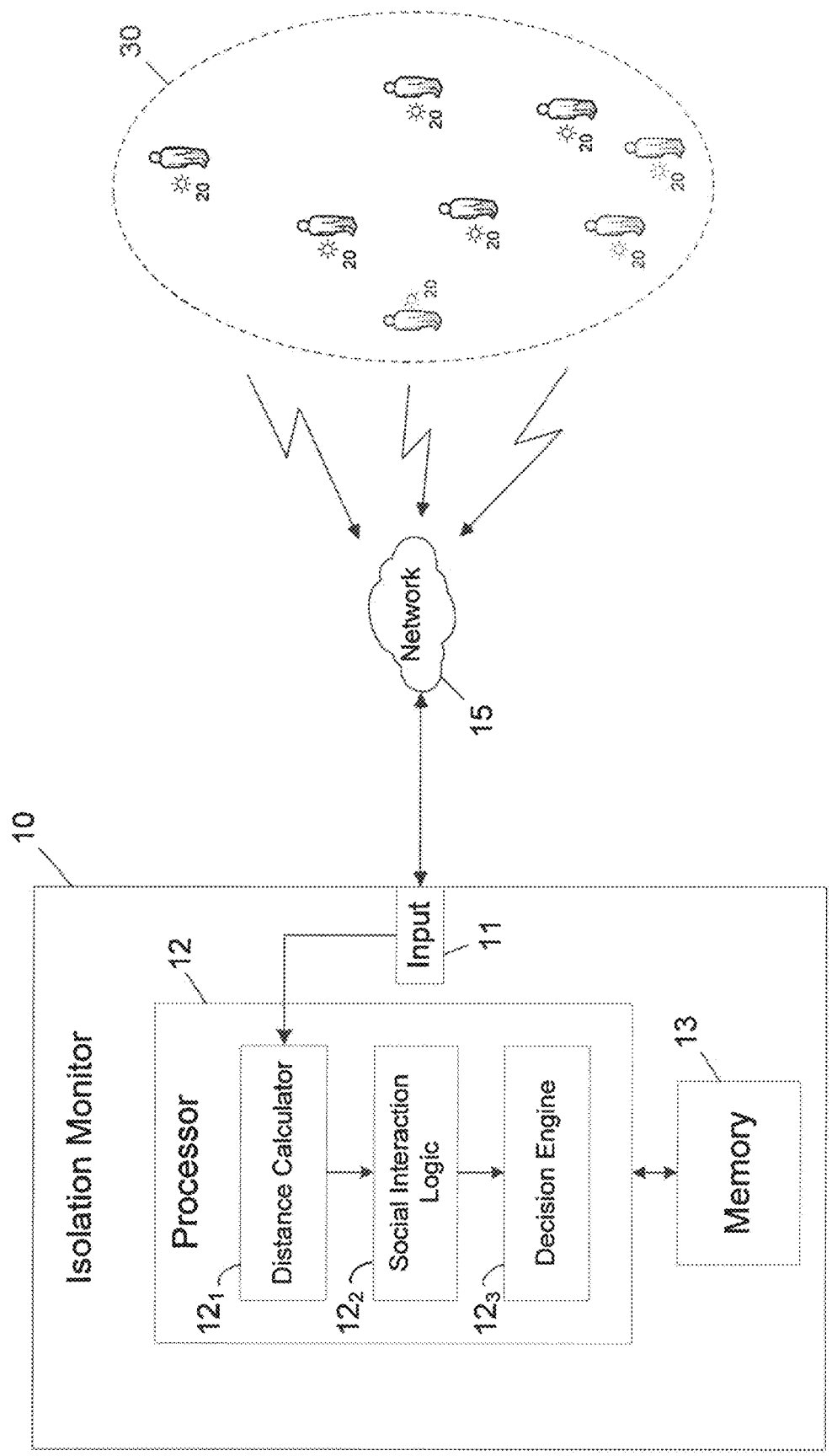
FIG. 1 illustrates an embodiment of a system for managing social isolated users.

It should be understood that the figures are merely schematic and are not drawn to scale. It should also be understood that the same reference numerals are used throughout the figures to indicate the same or similar parts.

The descriptions and drawings illustrate the principles of various example embodiments. It will thus be appreciated that those skilled in the art will be able to devise various arrangements that, although not explicitly described or shown herein, embody the principles of the invention and are included within its scope. Furthermore, all examples recited herein are principally intended expressly to be for pedagogical purposes to aid the reader in understanding the principles of the invention and the concepts contributed by the inventor(s) to furthering the art and are to be construed as being without limitation to such specifically recited examples and conditions. Additionally, the term, "or," as used herein, refers to a non-exclusive or (i.e., and/or), unless otherwise indicated (e.g., "or else" or "or in the alternative"). Also, the various example embodiments described herein are not necessarily mutually exclusive, as some example embodiments can be combined with one or more other example embodiments to form new example embodiments. Descriptors such as "first," "second," "third," etc., are not meant to limit the order of elements discussed, are used to distinguish one element from the next, and are generally interchangeable. Values such as maximum or minimum may be predetermined and set to different values based on the application.

Example embodiments correspond to a system and method for objectively monitoring social interactions for the purpose of identifying individuals experiencing loneliness, so that action may be taken for the purpose of improving quality of life. Unlike other approaches, the system and method implements a technical approach to identifying potentially lonely people within a same geographic area and then linking those people to generate interactions that otherwise would not be available through conventional approaches. In one or more embodiments, potentially lonely people are identified based on monitoring signals and/or sensor data and the severity of their loneliness is measured based on the generation of a social isolation score. This score for each individual may then be used as a basis for promoting interactions among those that are monitored by the system.

FIG. 1 illustrates an embodiment of a system which applies a technological approach to determining and managing socially isolated individuals in a given area. Socially isolated individuals may include, but are not limited to, elderly persons who have entered into a diminished pattern of social interaction. The diminished pattern of social interaction may be intentional on the part of the individuals or may be the consequence of sickness or other effects.

By monitoring these social interaction patterns, various types of information may be inferred using a model-based approach. For example, diminished social interaction patterns may provide a basis for determining increased risks of loneliness, which, if prolonged, may adversely affect mental health, quality of life and overall life expectancy. The diminished social interaction patterns may also provide a basis for inferring that associated individuals have one or more conditions (e.g., psychological disorders or other medical conditions which manifest in reduction in desired or engaged social interactions) that require attention. Once at-risk individuals have been determined, additional measures may be taken to ameliorate the risk and improve quality of life.

While the embodiments described herein are well-suited for elderly persons, other persons may also benefit. Examples include mentally challenged individuals (e.g., persons with Down's Syndrome, mental disabilities, cognitive disorders, etc.), persons diagnosed with post-traumatic stress syndrome or various forms of anxiety and depression, children who have been abused or suffered trauma of some kind of abuse, persons in rehabilitation centers or with a history of addiction who may be susceptible to relapsing when isolated, persons subject to non-conventional social conditions (e.g. individuals in correctional facilities, workers in isolated environments, communities isolated for long time under safety hazards, etc.).

Referring to FIG. 1, the system includes an isolation monitor 10 that receives signals from a plurality of user devices 20 through at least one communication system 15. The communication system may include one or a combination of 802.11-based networks, Bluetooth links, mobile communication systems, and/or other short-range, internet-based, or local area wired/wireless connections, to name a few. The type of communication system(s) used may correlate to the communication protocols operating in the user devices. In one embodiment, the user devices may have some type of unique identifier which allows the later user-specific distance determination to be performed. For illustrative purposes, the communication system 15 has been labeled with the term "network."

The user devices 20 may be any one of a variety of sensor-based devices for monitoring respective ones of a plurality of users located throughout a predetermined area 30. For example, the user devices may be on-body sensors or medical alert devices worn by their respective users. Examples include personal emergency response system (PERS) devices worn on the neck or wrist. Such devices may be equipped with radio frequency transceivers that perform, for example, WiFi or Bluetooth communications. Examples of these devices include, but are not limited to, those operating based on Philips Lifeline technology (e.g., GoSafe pendant, BlueWillow wristbands). In one embodiment, the user devices may be a smartwatch or smartphone application with location and/or medical sensors. The sensors may or may not operate in association with beacons located throughout the monitoring area 30. The location (and optionally other sensor) data may be transmitted to the isolation monitor for processing as described herein.

One embodiment may be tailored towards the use of WiFi-based mesh networks. In this case, each node may include a transmit and receive unit. The Bluetooth standard is another possibility that may be used in the context of ad hoc/mesh networks. In such embodiments, beacons/transmitters and locators/receivers may be used. In some cases, these and/or other different standards may be mixed in one or more alternative embodiments. The predetermined monitoring area 30 may include, for example, a nursing home, an assisted-living facility, an independent-living community, a rehabilitation center, or another area that includes subjects to be monitored. Within the monitoring area, the subjects may be located in one or more indoor locations (e.g., house(s), building(s), etc.), outdoor locations (e.g., park, school, etc.), or a combination of these locations. In one embodiment, the predetermined area may be a larger geographical region, such as but not limited to an apartment complex, residential area, or even a town or city, all of which may include subjects who pose a risk of isolation and thus are to be monitored in accordance with embodiments described herein.

The isolation monitor 10 includes an input 11, a processor 12, and a memory 13. The input 11 receives sensor data from the user devices in the monitoring area. The sensor data may include proximity information generated by the logic in each of the user devices 20. As discussed in greater detail below, the proximity information may be based on relative signal strength indicator (RSSI) values of respective ones of the user devices i.e. on the measurement of power in the received radio signals. In this case, the sensor data is received in the form of RF signals transmitted through the network. In one embodiment, the sensor data may include additional information indicative of vital signs, fall information, or other forms of environmental or health-related data.

The processor 12 executes instructions stored in the memory 13 for implementing one or more algorithms for determining the social isolation status of the user devices in the monitoring area. In order to determine social isolation status, the processor includes a distance calculator $12_1$, social interaction logic $12_2$, and a decision engine $12_3$. The distance calculator $12_1$ processes the proximity information in the received sensor data to calculate the locations of respective ones of the user devices. The locations may be determined relative to one another and/or relative to one or more reference points in the monitoring area. In one embodiment, the proximity information received from the user devices is in the form of a matrix containing values indicating relative distances between the user device that transmitted the proximity information and the other user devices in the monitoring area, as described in greater detail below.

The social interaction logic $12_2$ processes the location information output from the distance calculator to provide an indication of the social interaction experienced by the users in the monitoring area over a predetermined period of time. The social interaction of the users may be based solely on the location information or may be determined in combination with additional information, e.g., monitoring area layout, direction information, clustering information, additional sensor data, and/or other information.

The decision engine $12_3$ generates isolation decisions for the users based on the indications of social interaction generated by the social interaction logic. The isolation decisions may be binary in nature, indicating, for example, a probability that each of the users is in an isolated state warranting action or a non-isolated state requiring no immediate action. In various embodiments, the decision engine may generate scores indicating the relative degrees of isolation the users may be experiencing in the monitoring area over the observation period of time. This time period may be, for example, daily, weekly, monthly, or on a continual basis. The data received and generated by the isolation monitor may be stored in a database for use in performing trend analysis for the monitored users. Reports may then be generated along with notifications to family members, guardians, doctors, or other care professionals for helping users who have isolated themselves. The help may involve, for example, presenting opportunities or encouragement to increase the social interaction of isolated users with fellow users and/or the administration of mental and/or physical evaluations in order to determine health status or the possible onset of a disease.

Figure 2:
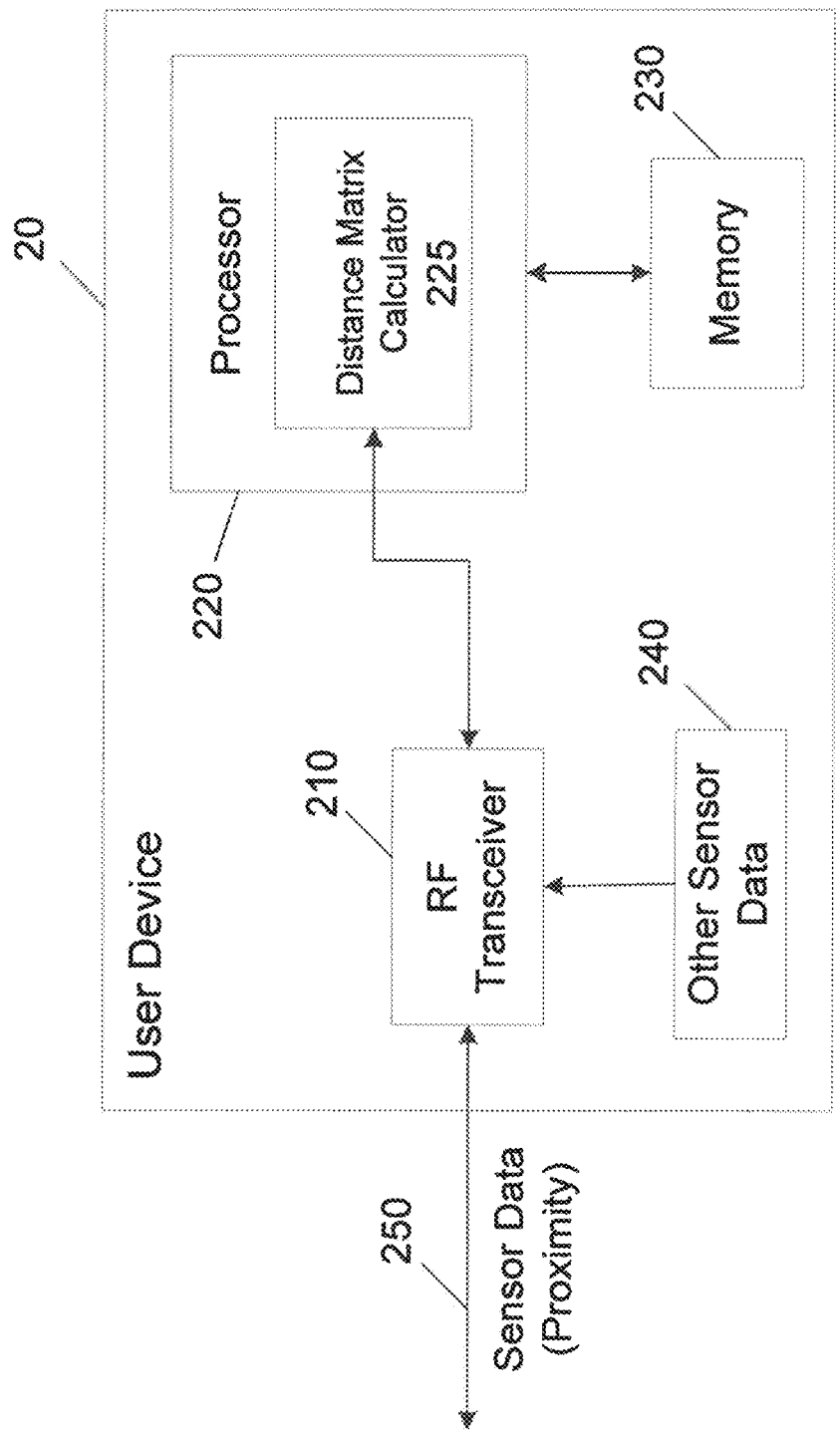
FIG. 2 illustrates an embodiment of a user device.

FIG. 2 illustrates an embodiment of how the user devices 20 in FIG. 1 may be configured for purposes of interacting with the isolation monitor. Referring to FIG. 2, each user device 20 may include an RF transceiver 210, a processor 220, and a memory 230. The RF transceiver 210 receives proximity information from other user devices in the monitoring area. The RF transceiver may perform this operation based on control software stored in the memory. This can be done automatically, periodically, or based on specific-user interaction with the device. This may be accomplished, for example, by the host device (e.g., smartphone) periodically scanning for WiFi access points. In one embodiment, results carried out during normal device use may be retroactively analyzed at the WiFi scans. The processor 220 processes the proximity information to generate proximity information relative to its own user device. For example, when the proximity information is expressed as RSSI values, the RSSIs for the other user devices in the monitoring area may be expressed by Equation 1:

$$R_{i,j} = \text{RSSI } j \text{ seen by } i;$$

$$i, j = 1 \ldots n \tag{1}$$

where i corresponds to the user device and j corresponds to the other user devices. The proximity information may then be transmitted to the isolation monitor through the RF transceiver.

Figure 4A:
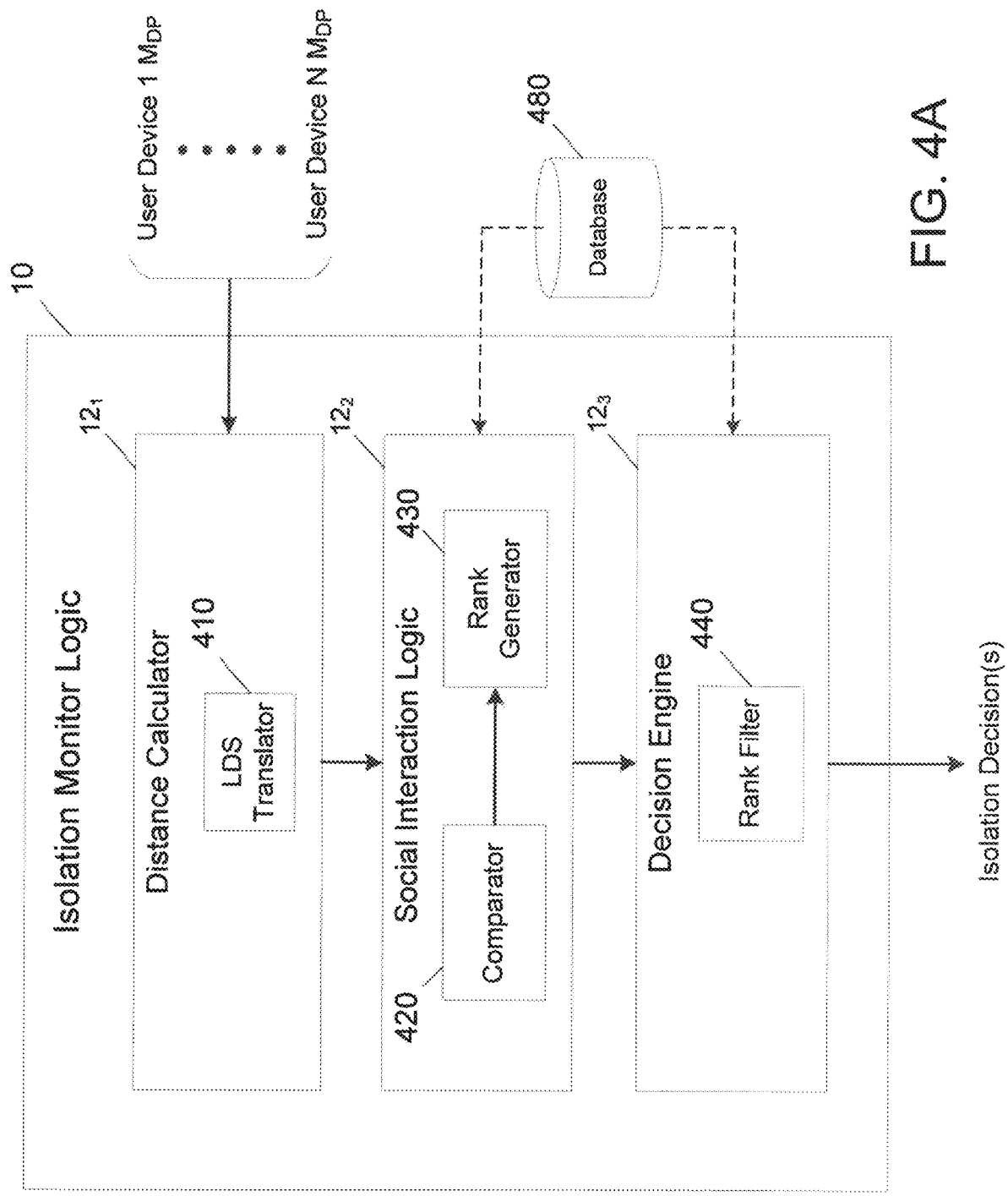
FIG. 4A illustrates an embodiment of isolation monitor logic.

The processor 220 may include a distance matrix calculator 225 for processing the proximity information based on instructions stored in memory 230. In one embodiment, the distance matrix calculator 225 generates distance pairs, with each pair representing a distance between the host user device and a respective one of the other user devices 20 in the monitoring area. In other embodiments, the distance matrix calculator is within the isolation monitor logic (FIG. 4A). These embodiments minimize that transmission of data between devices by means of a "hub" were the isolation monitor receives all data, shared between multiple user devices. This minimize also power consumption, memory and storage requirements at the individual devices which is desirable. These relative distance measurements may be calculated based on RSSI signals that correspond to the proximity information which the host user device receives from the other uses devices. Based on the magnitude of these RSSI signals, the distance matrix calculator is able to generate corresponding distances representing the distance pairs. The conversion from RSSI values to distance values may be determined based on an analytical relationship or may be obtained empirically, for example, by a calibration procedure.

In one embodiment, a monotonically decreasing relationship may be expected to exist between RSSI and distance, with a saturation phenomena and signal-to-noise ratio and consequent limits of detectability determined by environmental conditions. Values for the estimated distance may be further processed, for instance, by setting values below a certain RSSI threshold to distance 0, and values above another RSSI threshold to a comparative large distance value, that may be previously set. In one embodiment, the conversion from the RSSI values $R_{i,j}$ to distance values $d_{i,j}$ may be obtained based on function $f_{ESTIMATE}$, where the distance values may be expressed based on Equation 2.

$$d_{i,j}=f_{ESTIMATE}(R_{i,j}) \quad (2)$$

The aforementioned relationships and/or conversion calculations may be used as a basis for generating the distance pairs. For example, in one embodiment the distance between one specific user device and all other user devices (including itself, $d_{i,i}=0$) may be expressed as vectors with N distinct entries, as indicated in Equation 3.

$$D_1=[d_{1,1},d_{1,2}, \ldots d_{1,N}]$$

$$D_2=[d_{2,1},d_{2,2}, \ldots d_{2,N}]$$

$$\ldots$$

$$D_N=[d_{N,1},d_{N,2}, \ldots d_{N,N}]$$

Once generated, the distance pairs may be combined in at least one matrix that is transmitted (as proximity or sensor data 250) to the isolation monitor for processing. Alternatively the matrix can be calculated directly on the isolation monitor, by receiving the individuals RSSI from the user devices. The memory may be various versions of a non-transitory random access memory or read only memory. In one embodiment, the user device may include one or more detectors for detecting corresponding information relating to the user of the user device. This information may also be transmitted to the isolation monitor for processing in association with the distance pair matrix and/or in a manner independent from the distance pair matrix. The user device may also generate other sensor data 240 relating, for example, to the health or condition of the user and/or environmental conditions. The other sensor data may also be transmitted to the isolation monitor and/or one or more other predetermined locations.

Figure 3A:
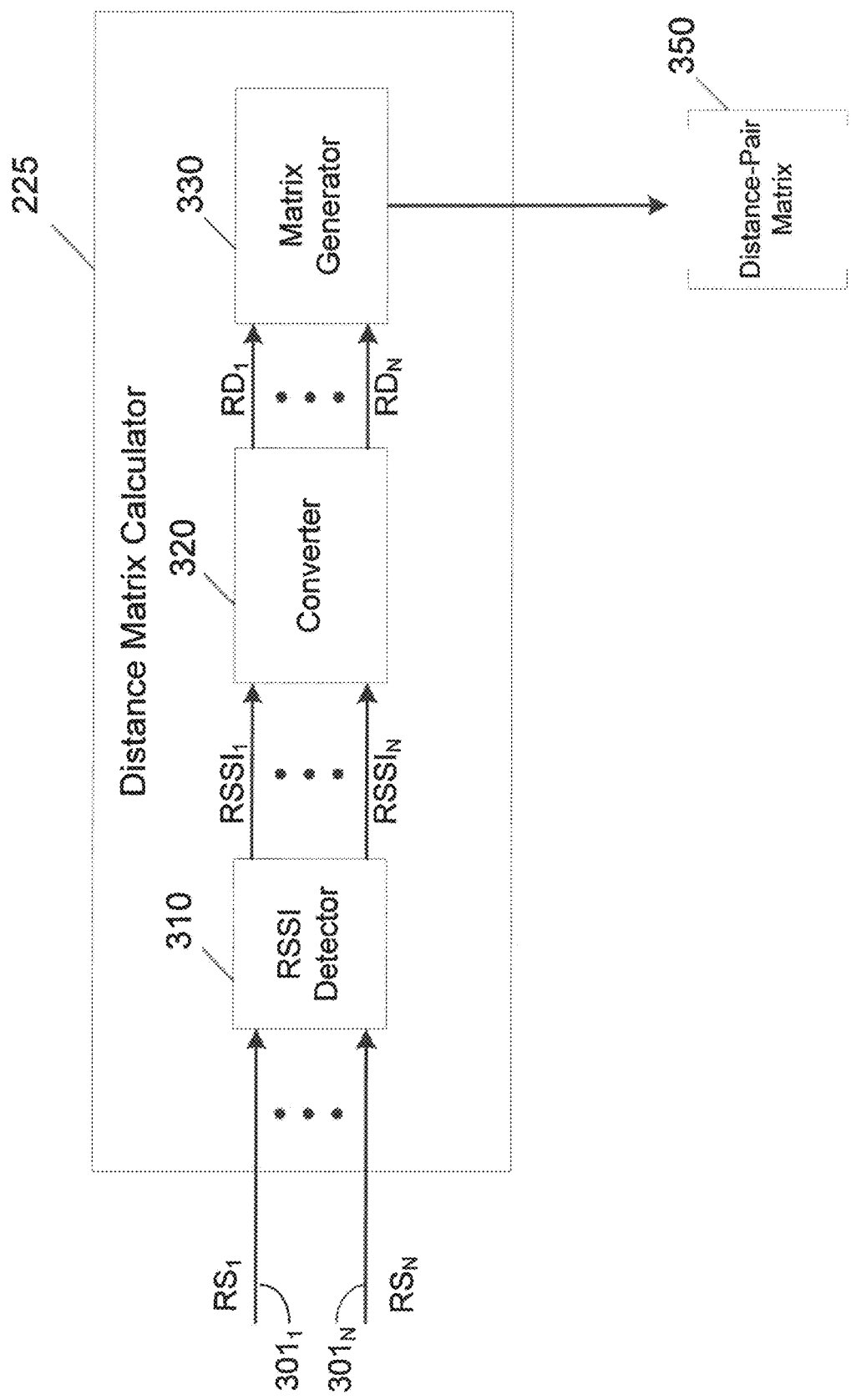
FIGS. 3A and 3B illustrate embodiments of a distance matrix calculators.

FIG. 3A illustrates an example of logic that may be used to drive an embodiment of an isolation monitor. The isolation monitor may be isolation monitor 10 of FIG. 1, which as previously described includes distance calculator $12_1$, social interaction logic $12_2$, and decision engine $12_3$.

Referring to FIG. 3A, the distance calculator $12_1$ includes an RSSI detector 310, a converter 320, and a matrix generator 330. The RSSI detector 310 receives signals $301_1$ to $301_N$ transmitted from the user devices in the monitoring area and determines their respective signal strengths $302_1$ to $302_N$ relative to the host user device, labeled $RSSI_1$ to $RSSI_N$. The received signals may be, for example, test signals, beacon signals, or identification signals.

The RSSIs may be determined, for example, by detecting the energy (or power) associated with the signals received from the user devices. In terms of the RF architecture, the RSSI values may be derived, for example, in the intermediate frequency (IF) stage of the receiver circuits of the user device prior to input into the IF amplifier. If the user device does not use an intermediate frequency, then the RSSI values may be determined in the baseband signal chain before the baseband amplifier. The RSSI value may be expressed, for example, as a DC analog level or an analog-to-digital converter may be used to sample the received signal to generate corresponding codes indicative of the user device RSSIs. In some embodiments, the received signals may include, or may be processed to determine, directional information. In this case, the received signals may be indicative of a vector. In one embodiment, signals $301_1$ to $301_N$ may be generated based on interactions of the host device using an RF communication protocol. In this case, device identifier information and RF power received information may be used. Also, one user device may be able to receive signals from other user devices in a variety of ways. For example, Bluetooth or WiFi devices may receive these signals from other user devices during operation, thereby in this case avoiding the need reprogram the user devices. Such signals may be received, for example, every time a receiver in the device scans for transmitters, such as when the receiver scans for WiFi access points.

Figure 3B:
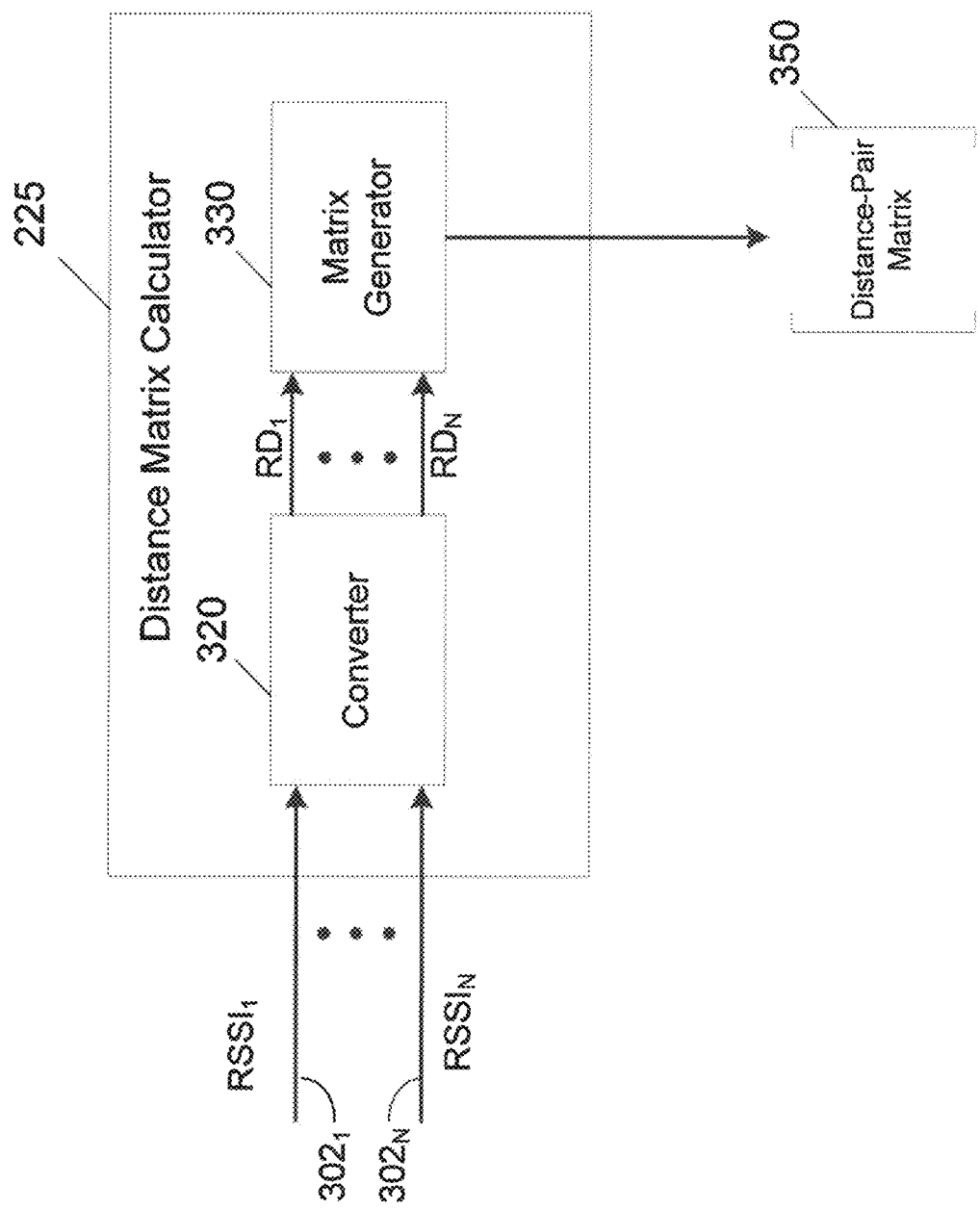

FIG. 3B illustrates another example of logic that may be used to drive an embodiment of an isolation monitor, which, for example, may be isolation monitor 10 of FIG. 1 including distance calculator $12_1$, social interaction logic $12_2$, and decision engine $12_3$. In this embodiment, labeled $RSSI_1$ to $RSSI_N$ Signals $302_1$ to $302_N$ are generated, for example, by the receiver (e.g., Bluetooth, WiFi, etc.) of the host device and input into the converter 320 of the distance matrix calculator 225. In such an embodiment, the RSSI detector 310 may be omitted.

The converter 320 converts the magnitudes of the RSSI values relative distance values, e.g., distances between relative ones of the user devices and the host user device receiving signals $301_1$ to 301N. The conversion may be performed, for example, as follows. Because of attenuation properties, the strengths of the received signals RS1 to RSN are proportional to (1) the distances between the user device and respective ones of the user devices that transmitted the received signals and (2) the power of the received signals. Because the transmitter power levels of the user devices are known (e.g., and may be the same), the relative distances 3031 to 303N (also labeled RD1 to RDN) may be estimated, for example, in accordance with Equation 4:

$$\text{Relative Distance}=10\char`\^((\text{Measured Power}-\text{RSSI})/(10*N)), \quad (4)$$

where N is a predetermined constant value that is dependent on an environmental factor.

The matrix generator 330 arranges the distance values output from the converter 320 into at least one matrix 350 ($M_{DP}$) having a predetermined format. Each entry of the matrix indicates the distance between the host user device and a corresponding one of the user devices in the monitoring area. As a result, a distance-pair matrix is formed. The format (and/or identification information associated with the matrix) allows the distance calculator of the isolation monitor to determine exactly what pairs are being referenced in the matrix, so that clusters or other groupings or outliers may be identified for input into the social interaction logic. Once the distance-pair matrix 350 is formed, it may be transmitted to the isolation monitor through the RF transceiver 210. The matrix may be generated on a periodic basis in response to a control signal generated by the user device. The control signal may be, for example, an enable signal, a power-up signal, or another signal generated by a controller of the user device. The controller may be programmed, for example, by system personnel to transmit distance-pair matrixes in order to comport with the requirements of the monitoring area.

In one embodiment, each user device 20 may store instructions in memory that controls its processor to transmit distance-pair matrixes (or other forms of distance data as may be the case in one or more other embodiments) to the isolation monitor on a periodic and/or event-driven basis. For example, each user device may transmit its distance-pair matrixes a predetermined number of times per day, e.g., once, twice, four times per day, hourly, based on a schedule, etc. In another implementation, the device may only transmit its own distance estimates/RSSI to the isolation monitor (e.g., it would transmit only one row/column of the distance matrix pair to be constructed by the isolation monitor). The isolation monitor may concatenate these rows/columns into a matrix. In one embodiment, each user device may transmit its distance-pair matrixes during times when social events are scheduled, during holidays, or other events. In this case, the instructions in each user device may be controlled, for example, based on a calendar application or other like data.

Figure 4B:
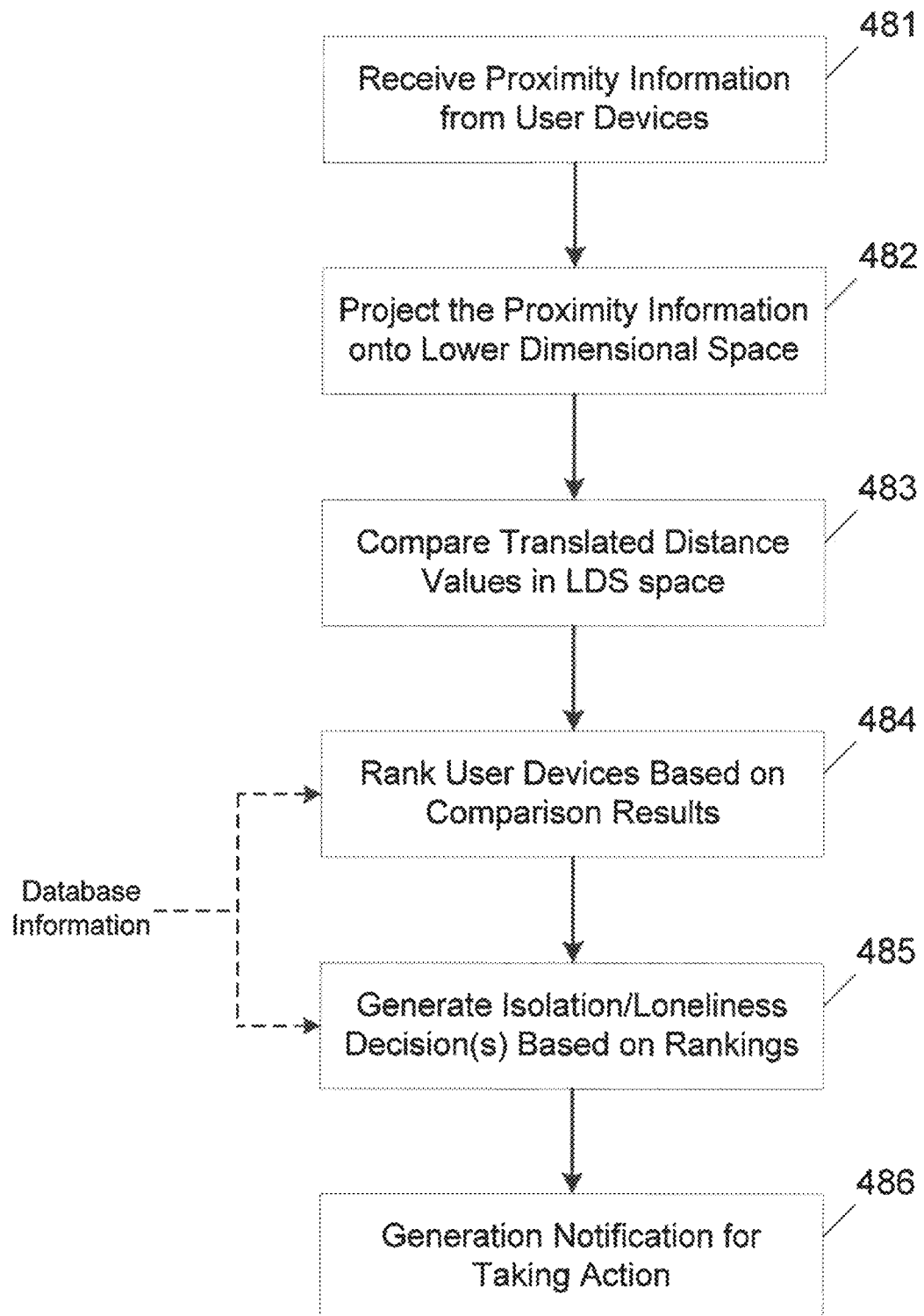
FIG. 4B illustrates an embodiment of a method performed by the isolation monitor logic of FIG. 4A.

FIG. 4A illustrates an embodiment of an isolation monitor, which, for example, may correspond to the isolation monitor 10 of FIG. 1. In the isolation monitor, the distance calculator $12_1$ includes a lower dimensional space (LDS) translator 410, the social interaction logic $12_2$ includes a comparator 420 and a rank generator 430, and the decision engine $412_3$ includes a rank filter 440. FIG. 4B illustrates an embodiment of a method which may be implemented by the isolation monitor of FIG. 4A.

Referring to FIGS. 4A and 4B, the lower dimensional space translator 410 receives proximity information in the form of distance-pair matrixes User Device 1 $M_{DP}$ to User Device N $M_{DP}$ from the user devices 20 in the monitoring area (Block 481) and then applies an algorithm to calculate a projection of the distance information from a high-dimensional space (as received) in the matrixes to a lower dimensional space (Block 482), with fewer dimensions. In one embodiment, a lower dimensional representation may be defined as a set of distinct vectors $X_{LDS,i}$, one per user i as indicated in Equation 5:

$$X_{LDS,i} = [X_1 \ldots X_m] \in R^M \quad (5)$$

with M<<N.

In one case, an LDS representation may be obtained as a result of multi-dimensional scaling, for example, by performing numerical optimization as indicated in Equation 6:

$$X_{LDS,1} \ldots X_{LDS,N} = \underset{X_{LDS,1} \ldots X_{LDS,N}}{\operatorname{argmin}} \sum_{i=1}^{N} \sum_{j=1}^{N} |\|X_{LDS,i} - X_{LDS,j}\| - D_{i,j}| \quad (6)$$

where $X_{LDS,1} \ldots X_{LDS,N}$ are projected distances for each user, $\|*\|$ indicates a distance metric (e.g., Euclidean, Manhattan, etc.), $|*|$ indicates a predetermined scalar error measure (e.g., absolute deviation, difference, squared differences, etc.) and $D_{i,j}$ are the individual entries of the pair-wise distance matrix derived from RSSI as in Equation 2. In one implementation, the dimensionality of the reduced space may be m, where M<<N, where N is the number of user devices in the monitoring area. For some applications, M=2 or M=3 but may be different for other applications. In some applications, M=N thus the projection can be an identify projection.

In many practical applications, the measured RSSI values for the user devices will change over time, for example, as a result of moving from one place to another, because of changing interference or environmental conditions, and/or because of other influences and effects. Taking these changes over time into account, each user device may measure the RSSI values of signals received from other user devices according to Equation 7.

$$R_{i,j}[t] = RSSI[t] \, j \text{ seen by } i \text{ at time } t \quad (7)$$

The LDS representation corresponding to Equation 6 is generated for one point in time (e.g., for a specific time t). However, like RSSI measurements, changes over time may also affect the conversion performed by the LDS translator 410. Taking this into account, the LDS translator 410 may generate LDS representations iteratively or at multiple times throughout the monitoring period. These representations may be combined to provide a time-varying LDS representation based on the projected distances $X_{LDS,i}[t]$, where I is a time variable, as indicated in Equation 8. In this case, Equation 6 may be rewritten based on Equation 8 to produce a time-varying LDS representation in the case of multi-dimensional scaling.

$$X_{LDS,i} = X_{LDS,i}[t] \quad (8)$$

In some embodiments, the algorithm applied by the LDS translator 410 may perform a linear transformation (e.g., using principle component analysis (PCA)) or a nonlinear dimensionality reduction technique, one example of which involves generating a tensor representation that can be used to perform dimensionality reduction through multilinear subspace learning. In another embodiment (e.g., as indicated above), a multi-dimensional scaling algorithm which preserves the pair-wise inter-user distances for each user device as much as possible. Additional translation techniques that may be performed by the LDS translator 410 include non-negative matrix factorization, manifold projection techniques, non-linear auto-encoding, or a combination of any of the foregoing techniques. The LDS translator 410 may continue to translate the information in the distance-pair matrixes as they are received, which, as previously indicated, may occur on a periodic or event-driven basis.

The comparator 420 receives the estimated distance values from the distance calculator and (not necessarily) those distances as expressed in the lower dimensional space relative to all of the user devices 20 in the monitoring area (Block 483). The comparator may indicate the minimum distance each user device is to the next-closest user device(s) and also remaining ones of the user devices. These results are then output to the rank generator 430, which ranks the user devices based on at least their minimum distances from the other uses devices over a monitoring time period (Block 484). The ranks may be expressed, for example, as a social isolation score, indicating a likelihood of the degree of interaction associated users may have based on the comparison results. The monitoring time period may be one day, one week, monthly, or another time period. Because distance-pair matrixes are being received multiple times from each device during the monitoring period, an accurate indication of user isolation patterns may be derived, which provides a basis for making isolation decisions by the decision engine. Once ranking results are computed, they are output to the decision engine either on a per-measurement basis or collectively over the monitoring period. If output on a per-measurement basis, the decision engine may collate and combine the results.

The rank filter 430 may apply a predetermined threshold to the ranking results over the monitoring period, to identify one or more user devices that may be considered at risk of suffering from loneliness (Block 485). In one embodiment, the predetermined threshold may correspond to one or a range of minimum distances that are sufficiently large as to prevent social interaction if maintained for a prolonged period of time, which may be a portion of or throughout all of the monitoring period (e.g., throughout the day, one or more weeks, a month, etc.).

Table 1 shows an example of inter-device distances of the user devices in the LDS space and their associated rankings. In Table 1, the users with the highest ranks are considered to be ones having the greatest loneliness risk. In another embodiment, the ranking may be performed so that the users with the lowest ranges are considered to be ones having the greatest loneliness risk.

TABLE 1

| User Device | Estimated Distance | Rank |
|---|---|---|
| 42 | 35 Feet | 1 |
| 21 | 28 Feet | 2 |
| N | 2 Feet | N |

In Table 1, all N user devices in the monitoring area have been ranked according to LDS inter-device distance. The ranking (e.g., by scores) is performed based on the user devices determined to have the largest values of minimum distance from other user devices. For example, over a predetermined time period (e.g., monitoring period), the average minimum distance between user device 42 and the next closest user device(s) was 35 feet. Since it is difficult the user of user device 42 to have any meaningful social interaction with another user when they are separated by 35 feet, the rank generator 430 has ranked user device 42 first. The average minimum distance between user device 21 and the next closest user device(s) was 28 feet. This distance was sufficient to rank user device 21 second. This ranking continues for all N user devices.

In this scenario, the rank filter 440 may apply a threshold set to then, meaning that the top ten ranked user devices may be considered at risk for loneliness. In one embodiment, the predetermined threshold may be set based on inter-device distance, e.g., all devices ranked with inter-device distances greater than 15 feet are considered to be at risk. The output(s) of the rank filter from the decision engine may cause the processor of the isolation monitor to generate an alarm or notification to prompt action, either from caregivers or family members, to remediate any isolation problems (Block 486).

In one embodiment, the isolation monitor may include a database 480 for storing information that may be taken into consideration by the rank generator 430 and/or the rank filter 440 when making ranking or isolation decisions. In one implementation, database 480 may store layout information of the monitoring area. The layout information may indicate the locations of walls, different rooms, floor plans, and/or other obstacles that may separate users, even when the distance between the users is relatively close. For example, the ranking engine 430 may retrieve information from the database to determine that two users are isolated from (or not socially interacting with) one another, even though their user devices are separated by only a few feet. This may occur, for example, when the users/user devices are in different rooms. Thus, the layout information stored in the database may change the rankings performed by the ranking generator from cases where such information is not taken into consideration, e.g., a user with a relatively low rank (indicating substantial social interaction) may be changed to a higher rank (indicating less social interaction) when the distance information and the layout information indicate that the user stays in his room all day and night.

The rank filter 440 may also take the information in database 480 into consideration when rendering decisions concerning isolation risk. For example, the rank filter may apply weights to the rankings in cases where users are determined to stay in their rooms all day, as opposed to users that are moving out of their rooms with at least some frequency during the day. The weights may have values that increase the ranking (e.g., trend toward ranking 1) the longer the user stays in his own room alone. In another example, weights may be given to change the rankings for users that receive visitors more often than other users. These weights may cause the rank filter to determine that the users are not at risk for being lonely, even though the users may not be around other users very much between visits. The weights may be applied in other ways depending, for example, on the particular application.

Figure 5A:
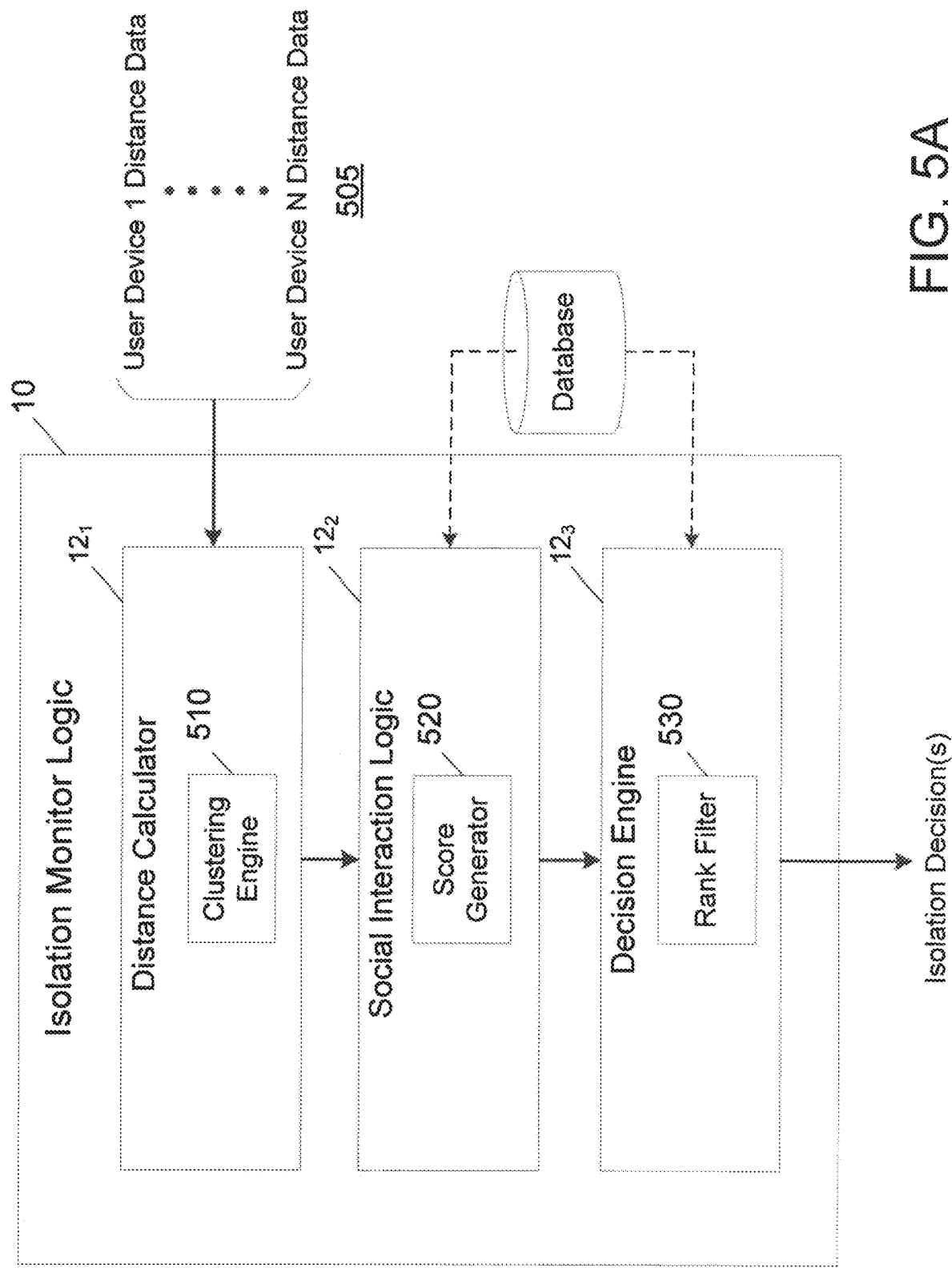
FIG. 5A illustrates an embodiment of isolation monitor logic.
Figure 5B:
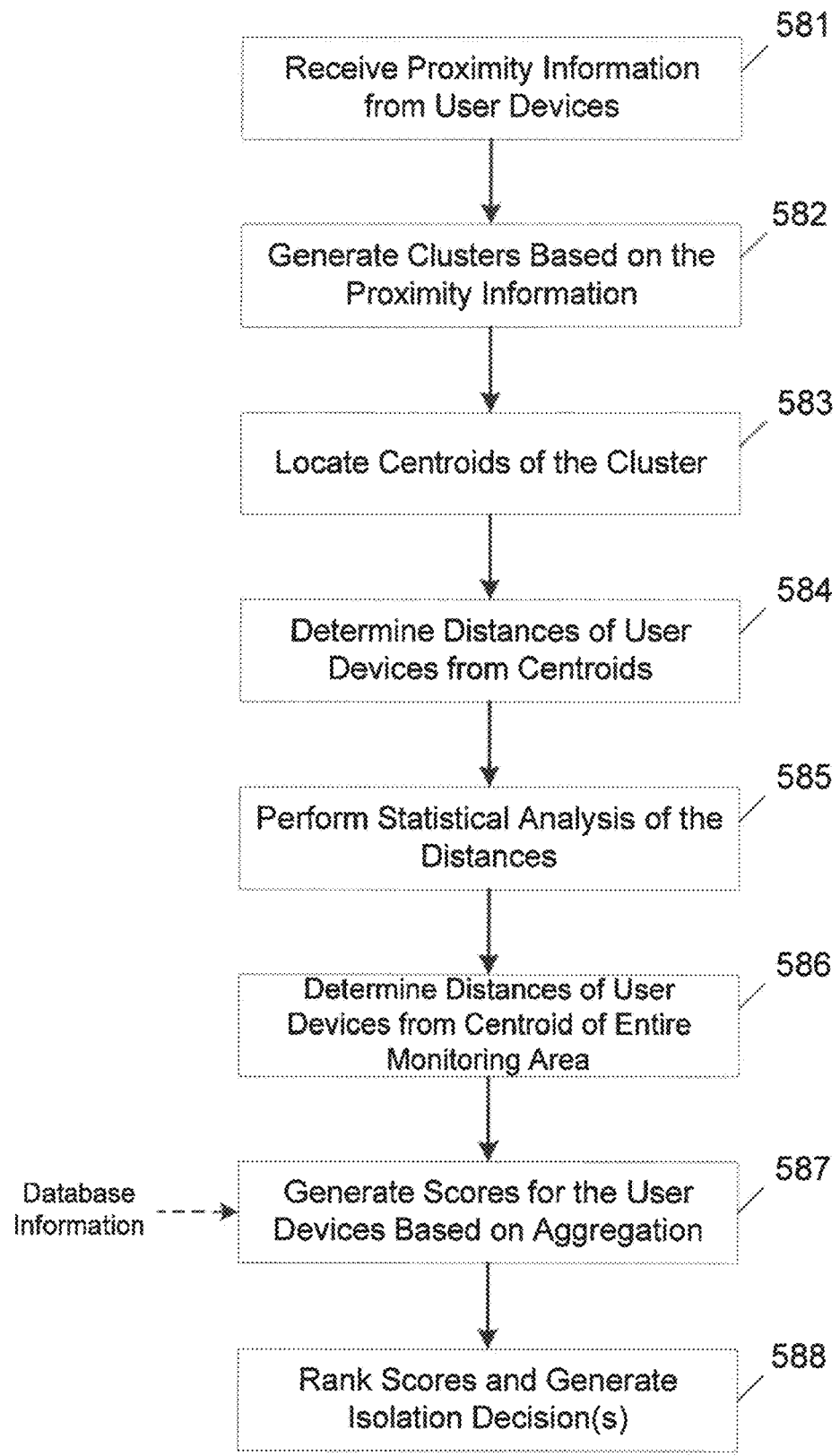
FIG. 5B illustrates an embodiment of a method performed by the isolation monitor logic of FIG. 5A.

FIG. 5A illustrates another embodiment of an isolation monitor, which, for example, may correspond to isolation monitor 10 in FIG. 1. In this embodiment, the distance calculator $12_1$ includes a clustering engine 510, the social interaction logic $12_2$ includes a score generator 520, and the decision engine $12_3$ includes a rank filter 530. FIG. 5B illustrates an embodiment of a method which may be performed by the isolation monitor of FIG. 5A.

The clustering engine 510 receives proximity (e.g., distance) information 505 (e.g., User Device 1 Distance Data to User Device N Distance Data) from the N user devices in the monitoring area over a monitoring period (Block 581). The distance information may provide an indication of the locations in the monitoring area of respective ones of the user devices. Thus, in this implementation the location information received from the user devices may not include distance-pair matrixes. In this case, the processor of each user device may execute instructions to transmit sensor data (including its own location) to the isolation monitor. In another embodiment, the distance information may include the distance-pair matrixes $M_{DP}$ as previously described. Also, in one embodiment an LDS translator may be included to convert the distance information 505 to a lower dimensional space before clustering is performed by the clustering engine 510.

The clustering engine 510 may execute one or more clustering techniques in order to generate a number of clusters from the received proximity (distance) information (Block 582). The number of clusters may be one or more. In one embodiment, clustering engine 510 may implement an unsupervised clustering technique using a gaussian-mixture-model or a k-means model which generates clusters of user devices (and thus users) existing throughout the monitoring area. Each cluster may include user devices that are spatially related, for example, within a given cluster size including at least a minimum number of user devices. The number of clusters may be determined automatically, for example, by methods such as Silhouette scoring. Each resulting cluster may be considered to be a "successful interaction network," e.g., ones where users of the user devices are socially interacting with at least a frequency that is considered to prevent the occurrence of an isolated or loneliness state. Information indicative of the clusters may then be output to scoring generator 520.

The scoring engine 520 may locate centroids within respective ones of the successful interaction networks (Block 583). This may be performed, for example, based on geographical or population weighted methods. Calculations may then be performed to determine the distances of the user devices in each cluster to its own centroid (Block 584). This may be performed, for example, based on the distance data received from respective ones of the user devices in each cluster, in comparison with the centroid location in that cluster.

Once the distances of the user devices is calculated, the average and standard deviation (SD) of those distances from the network centroid may be computed (Block 585). Then, the centroid of the entire monitoring area may be determined based on the locations of the centroids of the networks (Block 586). With this centroid known, the scoring engine may determine the distances of the user devices in all of the networks to the centroid of the entire monitoring area.

The score generator 520 may then aggregate the distances of the users devices from all networks using, for example, the mean or a smallest distance to the network centroids. The aggregated distances may then be normalized, for example, based on the previously calculated average and standard deviation. The normalized values may then serve as scores for corresponding ones of the user devices in the monitoring area (Block 587). These scores may then be output to rank filter 530.

The rank filter 530 may sort the scores in an order that indicate their corresponding rank, for purposes of generating an isolation decision (Block 588). For example, user devices with the highest scores (e.g., scores above a predetermined value) consistent over a period of time may indicate that corresponding users are at risk of loneliness and thus require attention. In one embodiment, scores higher than a threshold (e.g., 3) may be flagged to indicate isolation/loneliness risk. The threshold may change, for example, based for different values of aggregate distances or a desired level of sensitivity.

In some embodiments, clustering methods may be applied both on the original data (e.g., proximity information or distance data received from the user devices prior to LDS translation) and on the LDS projected data, with the latter being preferable for some applications in order to achieve higher robustness to "curse of dimensionality." Performing clustering on both the original and LDS projected data may, in some cases, produce a more accurate identification of successful interaction networks within the monitoring area. This identification may then be promoted depending, for example, on a cluster specific cohesion factor. In one embodiment, the clusters may be identified as groups of points with low intra-group distances and high-between-group distances. As with other embodiments, the score generator and/or the rank filter may take into consideration the layout information stored in database 550 of the monitoring area when generating the isolation decisions.

Figure 6A:
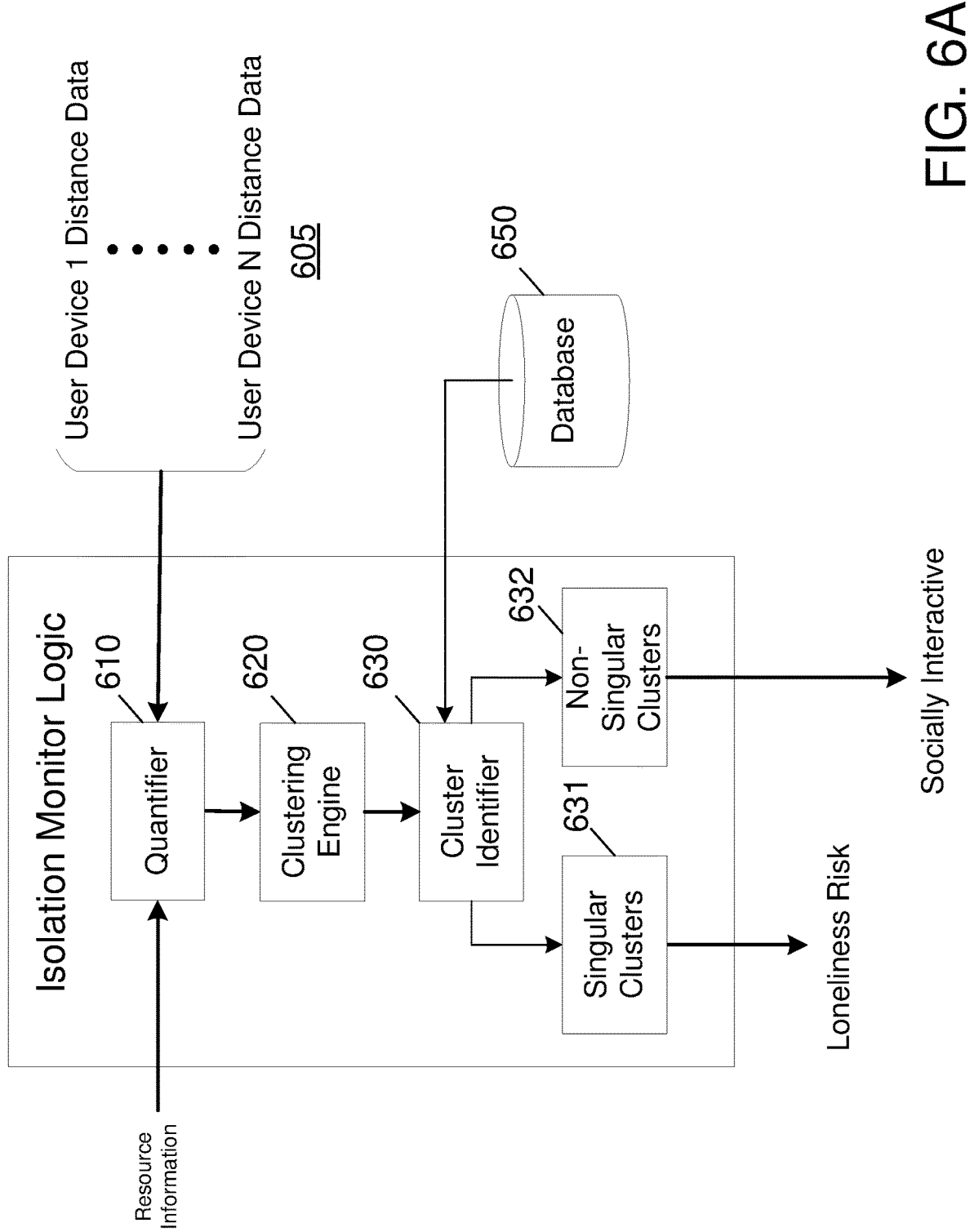
FIG. 6A illustrates an embodiment of isolation monitor logic.
Figure 6B:
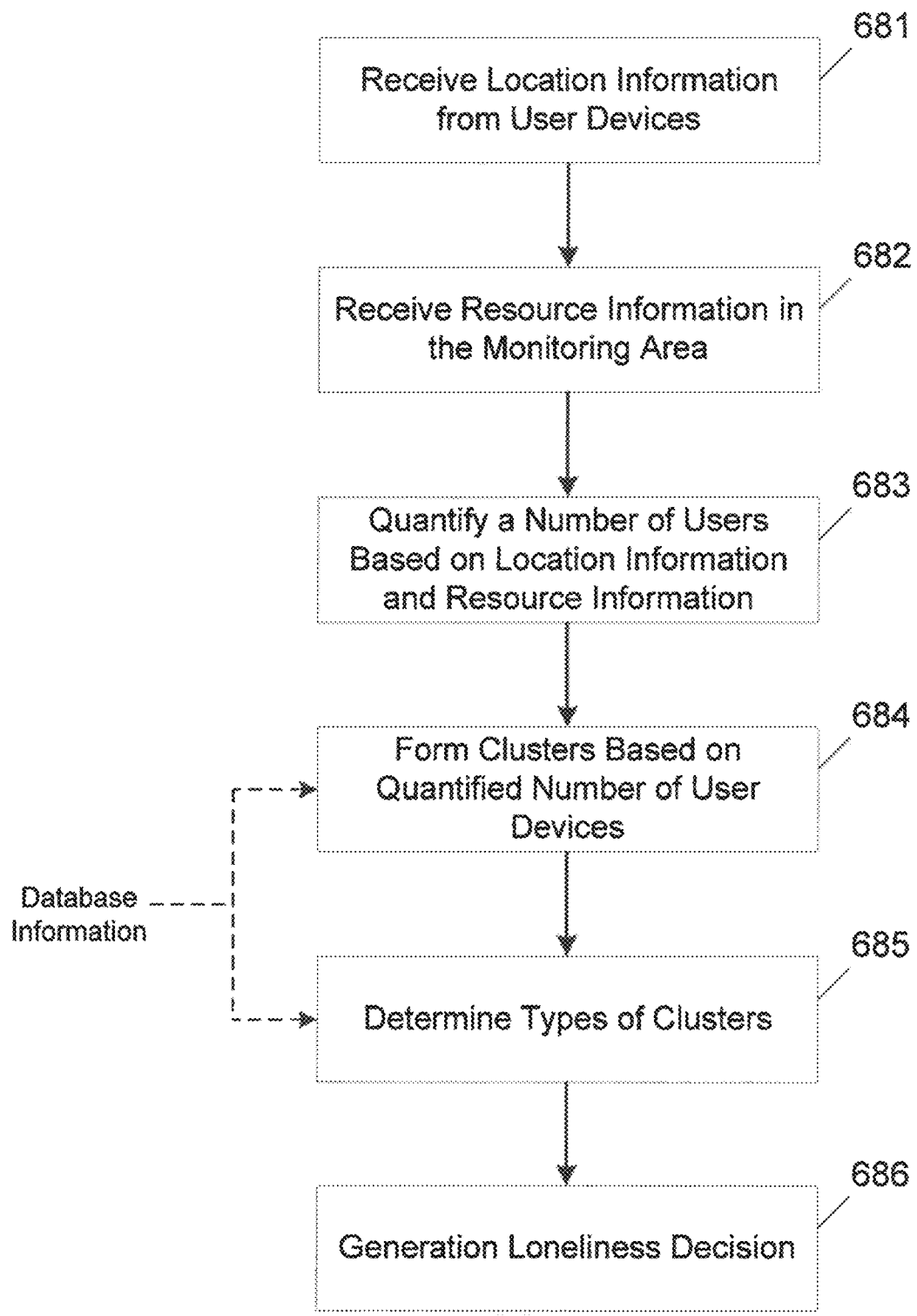
FIG. 6B illustrates an embodiment of a method performed by the isolation monitor logic of FIG. 6A.

FIG. 6A illustrates another embodiment of an isolation monitor which takes a resources-based approach to determining users at risk for loneliness. This embodiment of the isolation monitor includes a quantifier 610, a clustering engine 620, and a cluster identifier 630. FIG. 6B illustrates an embodiment of a method that may be performed by the isolation monitor of FIG. 6A.

The quantifier 610 receives distance information 605 (e.g., User Device 1 Distance Data to User Device N Distance Data) from the N user devices in the monitoring area over a monitoring period (Block 681), which may be as previously indicated. The distance information may provide an indication of the locations within the monitoring area of respective ones of the user devices. Thus, in this implementation the location information received from the user devices may not include distance-pair matrixes. In this case, the processor of each user device may execute instructions to transmit sensor data (including its own location) to the isolation monitor. In another embodiment, the distance information may include the distance-pair matrixes as previously described. In one embodiment, an LDS translator may be included to convert the distance information 605 to a lower dimensional space prior to input into the quantifier 610.

In addition to the distance information 605, the quantifier 610 receives resource information 608 indicating the amount of resources that are available for assisting users in the monitoring area (Block 682). The resource information may be provided, for example, by a server of a facility or system used to monitor activity in the monitoring area. The resource information may include the number of caregivers (e.g., doctors, nurses, volunteers, family members, etc.) presently available, the availability of services provided by the facility, the availability of rooms or meeting areas currently available, recreational activities, and/or other resources.

Based on the location information and the resource information, the quantifier determines (or quantifies) the number of users (corresponding to the user devices) for which there are resources to improve social interactions (Block 683).

The clustering engine 620 performs a top-down hierarchical clustering technique to form clusters based on information indicating the quantified number of users output from the quantifier (Block 684). These hierarchical clusters include both singular clusters and non-singular clusters. In one embodiment, the top-down hierarchical clustering technique may be applied in the following manner.

Initially, at a starting point, all device users may be assumed to be in one cluster. The sample with the highest average dissimilarity (e.g., farthest from the cluster by some metric) may then be reassigned to its own cluster. Any samples in the old cluster closer to the new cluster can then be assigned to the new cluster. These operations may be repeated with the largest cluster until each observation is its own cluster. Examples of metric functions include various types of distances (e.g. Euclidean distance, Malanhobis distance, Manhattan distance etc.). The clustering engine 620 stops splitting groups and/or sets a similarity cut through when the number of singular clusters reaches a predetermined number, which, for example, may correspond to the number of user devices in the monitoring area. In this context, dissimilarity scores used in the clustering algorithm may include spatial and/or temporal aspects derived from proximity information (e.g. estimated distances as in Table 2 arranged depending on the time t in Equation 8).

The clustering identifier 630 may identify the clusters generated by the clustering engine (Block 685). In one embodiment, the clustering identifier may identify the clusters as belonging on to one of two groups: singular clusters 631 and non-singular clusters 632. Singular clusters contain user devices (users) having highest levels of loneliness risk who require attention. Non-singular clusters may correspond to "successful interaction networks" containing users who are not at risk for loneliness, e.g., ones who are socially interactive. engine (Block 686). For these clusters, intra-cluster distance metrics are low e.g., the users are in cohesive group. As in other embodiments, the cluster 630 identifier may take into consideration the layout information stored in database 650 of the monitoring area in classifying clusters as singular or non-singular.

Figure 7:
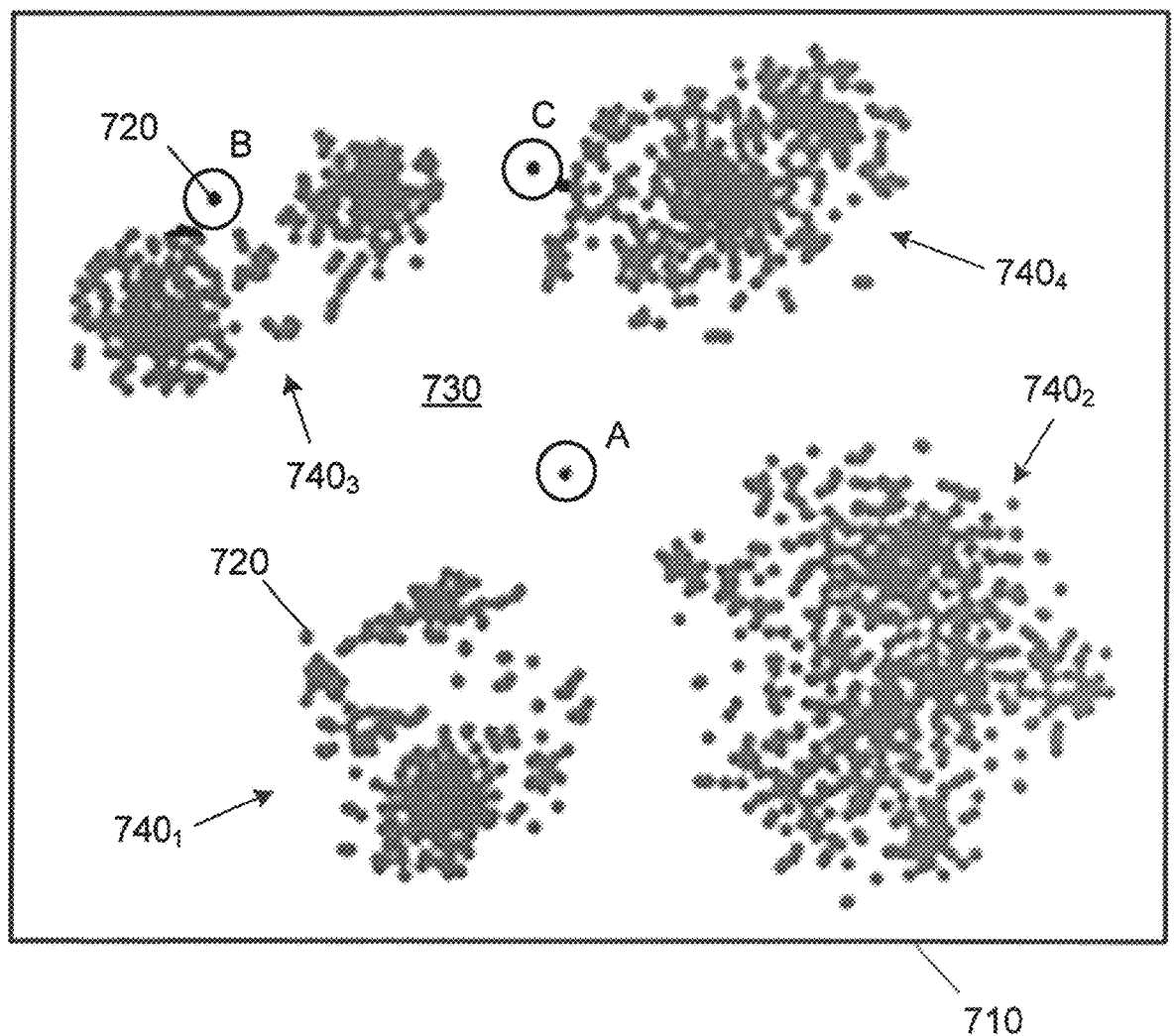
FIG. 7 illustrates a graphical representation of loneliness decisions in accordance with one or more of the aforementioned system and method embodiments.

FIG. 7 illustrates a graphical representation of the decisions generated by the various embodiments of the isolation monitor described herein. In this example, the graphical representation is in the form of a map 710 which includes dots corresponding to N users. Each user has his or her own user device 720 operating within the monitoring area 730. The coordinates of each dot may be given, for example, by multi-dimensional scaling of distance-pair measurements obtained with M=2.

When the isolation monitor performs clustering, the clusters may correspond to groupings $740_1$ to $740_4$. The user devices located in the groups are considered to be socially interactive and therefore not at risk for loneliness. However, the user devices that in circles A, B, and C correspond to users who have been identified by the isolation monitor for being at risk for loneliness.

In the map, user devices in circles B and C are relatively close to respective groups $740_3$ and $740_4$. Nevertheless, the users of these user devices may be flagged as exhibiting a socially isolated pattern over the monitoring period, warranting a decision by the isolation monitor of a risk for loneliness. This decision may be based on information indicating that the users of user devices in circles B and C are separated from the other nearby users by a wall, indicating that these users are staying alone in their rooms for extended periods of time. In one embodiment, the graphical representation illustrated in FIG. 7 may be displayed, for example, on a monitor of a facility supervisor or a website.

In addition to indications of loneliness, the embodiments described herein may be used to flag other conditions that may be associated with the decision of a user to maintain a pattern of isolation. These conditions may include medical reasons, including, but not limited to, undiagnosed dementia, Alzheimer's disease, or other forms of serious illness. When flagged for isolation, facility caregivers may screen these individuals to determine whether such medical conditions exist. Additionally, or alternatively, action may be taken by the facility in effort to increase the social interaction of those who have been indicated to be at risk for loneliness. In some embodiments, the action or intervention is delivered by means of a dedicated device (such as a virtual pet, or a robot, or a smart speaker or other device with conversational UI). The isolation pattern may be monitored to evaluate intervention adherence/efficacy.

In one embodiment, loneliness scores may be monitored and an alarm may be generated when the scores are outside of a predefined range for a predefined period of time. This range may correspond, for example, to scores that are in the top 10% for loneliness over the period of a week. Application and context-specific presets/cut-off values may be taken into account, for example, regarding the personal habits or a medical conditions (e.g., late-stage dementia, temporary health conditions such as infections).

In some embodiments, additional transmit or receive modules, not worn by the user and/or using a different communication standard (e.g., WiFi, Bluetooth, etc.) may provide additional contextual information to the individual devices, for instance, indoor positioning using Bluetooth beacons. Furthermore, layouts or housing plans may be used as a basis for increasing the accuracy of isolation decisions (for example, as previously discussed) using models for measuring RF signal absorption or reflection. These plans may also be used to initiate plausibility or room checks by facility caregivers or loved ones. In one embodiment, such information may be used at the stage of RSSI-to-distance conversion (e.g. assign maximum distance if two users are close but in different rooms, as they will not be interacting), as well as in score computation or other forms of isolation decision making (e.g., a measurement could be selected based on indoor location not, for example, to quantify loneliness scores only when users are in a certain room).

In one embodiment, not all RSSI measurements may be acquired simultaneously. In this case, the time(s) of interest during the monitoring period may be replaced by a time interval with a length, for example, that is negligible compared to expected time dynamics of changes in social isolation. For example, if changes are expected on a day-to-day basis, then RSSI measurements may be derived during a one-hour interval. In one embodiment, the distance values corresponding to the proximity information received from the user devices may be compared when those values are not in the LDS space, e.g., after the distances values have been translated out of the LDS space but before comparison (or the conversion to the LDS space may be omitted).

In one embodiment, users of the system may be divided in mutually exclusive groups and isolation score may be computed for each group separately. Each group could be a subpopulation of elderly users or groups could have different organizational roles (e.g., caregivers and patients in residents living facility). Different groups may be associated with different ranges of isolation and to different alarm rules. While the isolation monitor embodiments described herein have been indicated to receive proximity information directly from the user devices, the proximity information for the user devices may be received from one or more intervening devices which may collate or otherwise receive the proximity information from the user devices. Examples include a monitoring service, workstation, base station, server, router, or another type of intervening device or logic.

In accordance with one or more of the aforementioned embodiments, a system and method are provided to monitor interpersonal interactions of users of wearable sensors and/or other types of devices, in order to determine whether those users are at a risk for loneliness. These determinations may be made based on proximity information, which, for example, may correspond to received relative-signal strength indicator (RSSI)-based distance estimates obtained based on signals provided by the wearable devices. This information is then used as a basis for generating isolation decisions, which, for example, may be expressed in the form of social isolation scores.

Users identified at risk for loneliness may generate alarms or other notifications to facility supervisors, caregivers, loved ones, etc., to increase social interaction opportunities and/or extend emergency services or medical evaluations of the cognitive, social wellbeing, and/or physical state of the users. In one embodiment, the alarms or notifications may be sent to a guardian or family member (e.g., using Philips Cares) indicating a risk of loneliness and/or that the user is drifting away from social clusters, especially when such a user has recently lost a spouse or other person important in his or her life or at other critical or stressful times. In one embodiment, the social interaction scores may be generated for the purpose of standardized care assessment. Changes in social interaction scores may be subjected to trend analysis to indicate early signs of psychological disorders (e.g., depression) or cognitive decline (e.g., dementia).

The methods, processes, systems, and/or operations described herein may be performed by code or instructions to be executed by a computer, processor, controller, or other signal processing device. The code or instructions may be stored in a non-transitory computer-readable medium in accordance with one or more embodiments. Because the algorithms that form the basis of the methods (or operations of the computer, processor, controller, or other signal processing device) are described in detail, the code or instructions for implementing the operations of the method embodiments may transform the computer, processor, controller, or other signal processing device into a special-purpose processor for performing the methods herein.

The processors, monitors, calculators, logic, engines, converters, detectors, generators, filters, comparators, quantifiers, and other information generating, processing, and calculating features of the embodiments disclosed herein may be implemented in logic which, for example, may include hardware, software, or both. When implemented at least partially in hardware, processors, monitors, calculators, logic, engines, converters, detectors, generators, filters, comparators, quantifiers, and other information generating, processing, and calculating features of the embodiments may be, for example, any one of a variety of integrated circuits including but not limited to an application-specific integrated circuit, a field-programmable gate array, a combination of logic gates, a system-on-chip, a microprocessor, or another type of processing or control circuit.

When implemented in at least partially in software, processors, monitors, calculators, logic, engines, converters, detectors, generators, filters, comparators, quantifiers, and other information generating, processing, and calculating features of the embodiments may include, for example, a memory or other storage device for storing code or instructions to be executed, for example, by a computer, processor, microprocessor, controller, or other signal processing device. Because the algorithms that form the basis of the methods (or operations of the computer, processor, microprocessor, controller, or other signal processing device) are described in detail, the code or instructions for implementing the operations of the method embodiments may transform the computer, processor, controller, or other signal processing device into a special-purpose processor for performing the methods herein.

It should be apparent from the foregoing description that various exemplary embodiments of the invention may be implemented in hardware. Furthermore, various exemplary embodiments may be implemented as instructions stored on a non-transitory machine-readable storage medium, such as a volatile or non-volatile memory, which may be read and executed by at least one processor to perform the operations described in detail herein. A non-transitory machine-readable storage medium may include any mechanism for storing information in a form readable by a machine, such as a personal or laptop computer, a server, or other computing device. Thus, a non-transitory machine-readable storage medium may include read-only memory (ROM), random-access memory (RAM), magnetic disk storage media, optical storage media, flash-memory devices, and similar storage media and excludes transitory signals.

Although the various exemplary embodiments have been described in detail with particular reference to certain exemplary aspects thereof, it should be understood that the invention is capable of other example embodiments and its details are capable of modifications in various obvious respects. As is readily apparent to those skilled in the art, variations and modifications can be affected while remaining within the spirit and scope of the invention. The embodiments may be combined to form additional embodiments. Accordingly, the foregoing disclosure and figures are for illustrative purposes only and do not in any way limit the invention, which is defined only by the claims.

We claim:

1. A method for managing information, comprising:
   receiving proximity information for a plurality of user devices;
   projecting the proximity information into a lower dimensional space as distance values for each of the plurality of device;
   comparing the distance values of the plurality of user devices that correspond to the proximity information;
   ranking the plurality of user devices based on results of the comparison; and
   generating a loneliness decision for a user of at least one of the plurality of user devices based on the ranking of the user devices, wherein ranking the plurality of user devices includes:
   receiving layout information for a monitoring area including the plurality of user devices, and
   adjusting the ranking of one or more of the plurality of user devices based on the layout information.

2. The method of claim 1, wherein:
   the proximity information includes at least a set of pair-wise distance values, and
   the pair-wise distance values indicate distance estimated between a first user device of the plurality of user devices and remaining ones of the plurality of user devices, respectively.

3. The method of claim 2, wherein the pair-wise distance values are based on received radio frequency (RF) power.

4. The method of claim 1, wherein ranking the plurality of user devices includes:
   assigning scores to the plurality of user devices based on results of the comparison,
   wherein each of the scores provides an indication of a social interaction pattern of a user of a corresponding one of the plurality of user devices in a monitoring area during a monitoring period.

5. The method of claim 4, wherein generating the loneliness decision includes:
   applying a threshold to the scores of the plurality of user devices, and
   determining that the user of at least one user device is at risk for loneliness based on the applied threshold.

6. The method of claim 1, wherein adjusting the ranking of one or more of the plurality of user devices based on the layout information includes:
   assigning scores to the plurality of user devices based on results of the comparison and the layout information, wherein the layout information indicates at least one of a wall or room occupied by the user of the at least one of the plurality of user devices.

7. The method of claim 1, further comprising:
generating a notification indicating that the user of the at least one of the plurality of user devices requires assistance to increase social interaction or requires a medical health evaluation.

* * * * *